United States Patent [19]
Hill

[11] Patent Number: 6,075,158
[45] Date of Patent: Jun. 13, 2000

[54] TRANSESTERIFICATION PROCESS

[75] Inventor: Jonathan Simon Hill, Manchester, United Kingdom

[73] Assignee: Great Lakes Chemical Corporation, West Lafayette, Ind.

[21] Appl. No.: 08/776,972

[22] PCT Filed: Aug. 9, 1995

[86] PCT No.: PCT/GB95/01883

§ 371 Date: Jul. 21, 1997

§ 102(e) Date: Jul. 21, 1997

[87] PCT Pub. No.: WO96/05208

PCT Pub. Date: Feb. 22, 1996

[30] Foreign Application Priority Data

Aug. 10, 1994 [GB] United Kingdom .................. 9416334

[51] Int. Cl.⁷ ............................. C07F 9/12; C07F 9/11; C07F 9/09
[52] U.S. Cl. ............................. 558/118; 558/119
[58] Field of Search ..................... 558/118, 119

[56] References Cited

U.S. PATENT DOCUMENTS

| | | | |
|---|---|---|---|
| 2,557,089 | 6/1951 | Gamrath et al. | 260/30.6 |
| 2,596,141 | 5/1952 | Gamrath et al. | 260/461 |
| 2,805,240 | 9/1957 | Prahl | 260/461 |
| 3,272,892 | 9/1966 | Szabo | 558/119 |
| 3,414,639 | 12/1968 | Hodan et al. | 558/118 X |
| 3,422,453 | 1/1969 | Frank | 558/118 |
| 4,305,789 | 12/1981 | Prahl | 203/14 |
| 4,438,048 | 3/1984 | Finley | 260/982 |
| 4,443,384 | 4/1984 | Finley | 260/982 |
| 4,482,506 | 11/1984 | Finley et al. | 558/119 |

FOREIGN PATENT DOCUMENTS

| | | |
|---|---|---|
| 0143448 A2 | 9/1985 | European Pat. Off. . |
| 2215722 | 9/1989 | United Kingdom . |

OTHER PUBLICATIONS

JACS 85, No. 22, Nov. 20, 1963 3533–3539 PCT.
Ogilvie, K.K. and S.L. Beaucage. "Fluoride Ion–promoted Transesterification in Phosphate Triesters." J. Chem. Soc. Chem. Commun., 443, Jul. 1976.

*Primary Examiner*—Michael G. Ambrose
*Attorney, Agent, or Firm*—Woodart, Emhardt, Naughton Moriarty & McNett

[57] ABSTRACT

A process for the preparation of a phosphate ester is disclosed. A triaryl phosphate is reacted with an alcohol in the presence of a catalytic quantity of a base to produce the phosphate ester product. The base has a base strength of less than 11, and is preferably potassium fluoride or potassium carbonate. Trialkyl phosphates, dialkyl monoaryl phosphates, monoalkyl diaryl phosphates, and mixtures of these compounds can be produced by this process.

32 Claims, No Drawings

TRANSESTERIFICATION PROCESS

This application is filed under 35 U.S.C. § 371 and is the National Stage of International Application No. PCT/GB95/01883, filed Aug. 9, 1995.

This invention relates to a novel process for the production of esters of oxyacids of pentavalent phosphorus by the transesterification of an ester of such an oxyacid of phosphorus with an alcohol or phenol. In a first preferred embodiment the invention provides a process for the production of triakyl, dialkylphenyl and alkyldiphenyl phosphates by the transesterification of triphenyl phosphate with an aliphatic alcohol. In a second preferred embodiment the invention provides a process for the production of tris (alkaryl) phosphates by the transesterification of triphenyl phosphate with an alkylated phenol.

BACKGROUND OF THE INVENTION

A large number of esters oxyacids of pentavalent phosphorus are produced as articles of commerce e.g. phosphates, thiophosphates and phosphonates. The majority of them are produced by the reaction of an alcohol or phenol with phosphorus oxychloride or with a chloridate. Such reactions are inherently disadvantageous in so far as they involve the handling of chlorine or a derivative thereof.

The present invention finds particular application to processes for the production of phosphate esters. Triaryl phosphates are produced in large quantities by the reaction of phenol or alkyl substituted phenols or a mixture of such phenols with phosphorus oxychloride. Monoalkyl diaryl phosphates are produced by the reaction of phosphorus oxychloride with one molar proportion of an alcohol and the subsequent reaction of the dichloridate produced with a phenate anion.

There have been proposals to produce mixed alkylaryl phosphate esters by the transesterification of a triaryl phosphate such as triphenyl phosphate with an aliphatic alcohol. Finley, U.S. Pat. No. 4,443,384, discloses carrying out such a transesterification by initially adding aqueous sodium hydroxide to the alcohol to form an alkoxide and subsequently reacting that alkoxide with the triaryl phosphate. Finley, U.S. Pat. No. 4,482,506, discloses carrying out such a transesterification in the presence of a phenoxide catalyst. The phenoxide is stated to function by virtue of interacting with the alcohol to generate an alkoxide and the reaction is effected by initially reacting the phenoxide with the alcohol and subsequently adding the triaryl phosphate. None of these proposals has been entirely successful in producing a high yield of alkyl aryl phosphate (i.e., a product containing only small amounts of unreacted triaryl phosphate) and all suffer from a tendency towards by-product formation and concomittant catalyst deactivation. The manufacture of phosphate esters has continued to be practised on a large scale using phosphorus oxychloride or a chloridate as a raw material despite the attendant disadvantages thereof.

SUMMARY OF THE INVENTION

We have now discovered that the transesterification of an ester of an oxyacid of pentavalent phosphorus with an alcohol or phenol can be carried out efficiently in the presence of a catalytic quantity of a base B having a base strength (expressed as the $pK_a$ of the conjugate acid $BH^+$) of less than 11.

DETAILED DESCRIPTION OF THE INVENTION

In this specification the base strength of a base B is defined by reference to the equilibrium $$B+H^+ = BH^+$$

wherein the base strength is defined as $-\log_{10} Ka$ of the conjugate acid $BH^+$ where $Ka = \dfrac{[B][H^+]}{[BH^+]}$ and these concentrations are measured in aqueous solution at 25°.

Bases having a base strength of greater than 11 (such as alkoxide which has a base strength of approximately 14) have been found to be less effective in so far as they tend to promote competing reactions. This not only reduces the yield of the desired product but also leads to the poisoning of the basic catalyst by acidic products of these competing reactions. The milder bases having a base strength of less than 11 have been discovered to be more selective in favouring the transesterification reaction and more active apparently due at least in part to the reduced quantities of acidic by-products which are generated in the presence of these milder bases. Previous attempts to use milder bases such as phenoxide as a catalyst for the reaction (phenoxide typically has a base strength of approximately 9.95) such as are described in U.S. Pat. No. 4,482,506 involving the reaction between triphenyl phosphate and an aliphatic alcohol such as 2 butoxy ethanol have required that the phenoxide is reacted with the alcohol as an initial step. The processes of this invention are distinguished from those of U.S. Pat. No. 4,482,506 by the requirement that when the process is one for the production of a monoalkyl diphenyl phosphate by the reaction of triphenyl phosphate with 2-butoxy ethanol and the catalyst is phenoxide, the phenoxide is not initially reacted with the 2-butoxy ethanol.

Accordingly in one aspect this invention provides a process for the production of a first ester of an oxyacid of pentavalent phosphorus by the transesterification of a second ester of an oxyacid of pentavalent phosphorus with an alcohol or phenol which is characterised in that the reaction is carried out in the presence of a catalytic quantity of a base having a base strength of less than 11 with the proviso that where the second ester is triphenyl phosphate, the alcohol or phenol is 2-butoxyethanol and the catalyst is the phenoxide anion, the phenoxide is not initially reacted with the 2-butoxyethanol.

The transesterification reaction requires that the leaving group which is displaced from the second ester is a better leaving group than the nucleophilic species derived from the alcohol or phenol (or that the leaving group is sufficiently volatile to allow it to be continuously removed from the reaction medium). The knowledge as to which transesterification reactions are capable of proceeding to produce useful amounts of product is within the purview of the person skilled in the art and can be determined by routine experiment.

The catalysts which are useful in the processes of this invention may be selected from those having a base strength (as hereinbefore defined) of less than 11. Preferably the catalyst has a base strength in the range of 2 to 11 and most preferably in the range 3 to 8. Examples are certain amines, acetates, phenoxides, carbonates, phosphites, hypophosphites, bicarbonates, phosphates, tungstates , oxides and fluorides. Many of these useful catalysts are so called 'hard bases'; the term 'hard bases' being used in the sense described by R. G. Pearson in the Journal of the American Chemical Society, volume 85, 3533, 1963 and elaborated elsewhere notably in the monograph 'Hard and Soft Acids and Bases' by R. G. Pearson, published by Dowden Hutchinson and Ross Stroudsbury Pennsylvania 1973. These bases are anionic in character and the nature of the counter cation may exert an effect upon the activity of the base as a catalyst for the transesterification reaction. We have discovered that catalysts which are hard bases may be more effective catalysts in the processes of this invention and processes which use hard bases represent a preferred embodiment of this invention. The processes of this invention have been discovered to essentially involve a homogeneous reaction and the effectiveness of any particular catalyst in any particular reaction varies with its solubility in the reaction medium. The utility of any particular material to catalyse any particular transesterification may be determined by experiment.

Examples of catalysts certain of which may be useful in the processes of this invention include alkali metal fluorides especially potassium fluoride, rubidium fluoride and cesium fluoride; alkaline earth metal fluorides and the transition metal fluorides; the alkali metal carbonates especially potassium carbonate, cesium carbonate and ammonium carbonate; alkaline earth metal carbonates especially barium carbonate and strontium carbonate; the rare earth metal carbonates especially lanthanum carbonate and cerium carbonate; metal acetates especially potassium acetate, zinc acetate, cupric acetate and stannous acetate; alkali metal hypophosphites especially sodium hypophosphite and potassium hypophosphite; metal phosphates especially calcium phosphate; solid oxides such as calcium oxide, magnesium oxide, nickel oxide, strontium oxide and hydroxyapatite; organic bases such as alkylamines especially ethylamine, diethylamine, dimethylamine, pyridine, pyrollidine, piperidine, morpholine, quinoline, imidazole, quinuclidine, DABCO, DBU and DBN.

The preferred process of the present invention may be described as processes for the production of a compound having the general formula I

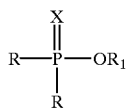

by the reaction of a compound having the general formula II

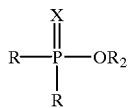

with an alcohol or phenol having the formula $HOR_1$ in the presence of a catalytic quantity of a base having a base strength of less than 11 wherein X represents an oxygen atom or a sulphur atom; the groups R which may be the same or different represent an alkyl or alkenyl group comprising from 1 to 24 carbon atoms; an aryl group or an alkyl substituted aryl group wherein the alkyl substituent comprises from 1 to 18 carbon atoms or a group —OR wherein R is as hereinbefore defined and $R_1$ and $R_2$ which may not be identical and which may not represent a hydrogen atom may otherwise represent any of the Groups R.

The groups R may be substituted or unsubstituted. In some preferred embodiments they are unsubstituted. In other preferred embodiments they may comprise one or more substituents selected from the group comprising hydroxyl groups; alkoxy groups having the formula $—OR_4$ wherein $R_4$ represents an alkyl or alkenyl group comprising from 1 to 24 carbon atoms; a halogen atom or a group having the formula —P(X)RR wherein R is as hereinbefore defined.

Particular classes of esters of oxyacids of pentavalent phophorus having the general formula II which may be used in the processes of this invention include compounds having the general formulae III, IV, V, and VI wherein R and $R_2$ are as hereinbefore defined.

PHOSPHATES

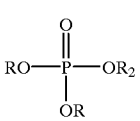

III

THIOPHOSPHATES

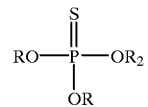

IV

PHOSPHONATES

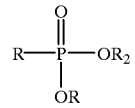

V

PHOPHINATES

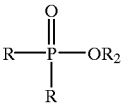

VI

A preferred group of esters for use as starting materials are the phosphate esters having the Formula III wherein the groups R all represent aryl groups and in particular benzyl groups and/ or akyl substitited benzyl groups wherein the alkyl substituent comprises 3 or 4 carbon atoms. Particular examples of esters of general formula III which may be used in the processes of the present invention include triphenyl phosphate, tricresyl phosphate, cresyl diphenyl phosphate, trixylyl phosphate, tris (isopopyl phenyl) phosphate, tris (t-butyl phenyl) phosphate, mixtures of triaryl phosphate esters which have been produced by the reaction of phosphorus oxychloride with a mixture of phenols and alkylated phenols and tris (2,4-dibromo phenyl) phosphate.

A second preferred group of esters for use as starting materials in the processes of this invention are the phosphate esters having the formula III wherein the groups R all represent alkyl groups comprising from 1 to 18 carbon atoms specific examples being tris (trichloroethyl) phosphate, triethyl phosphate, tributyl phosphate, tris (butoxyethyl) phosphate and trioctyl phosphate.

Particular examples of esters of the Formula V or VI which may find use as strating materials in the processes of this invention include diphenyl methane phosphonate, diphenyl phenyl phosphonate, dicresyl methyl phosphonate, dimethyl methane phosphonate, diethyl ethane phosphonate, phenyl dimethane phosphinate and methyl dimethane phosphinate.

Esters of oxyacids of pentavalent phosphorus acids which comprise more than one phosphorus atom as part of their molecular structure may also be used as starting materials in the processes of this invention. A preferred group of such esters are the phosphates of Formula III wherein at least one group R is substituted by a P(O)RR group. Such esters may include those having the general formula VII.

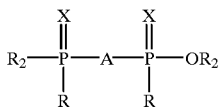

wherein A represents a divalent organic group especially a benzyl group, an alkylene group comprising from 1 to 4 carbon atoms, or a sulphonyl group —$SO_2$—, and $R_2$ and R are as hereinbefore defined. Specific examples of such esters include resorcinol tetraxylyl diphosphate, resorcinol tetraphenyl diphosphate, hydroquinone tetraphenyl diphosphate, resorcinol tetracresyl diphosphate, hydroquinone tetraxylyl diphosphate and bisphenol A tetraphenyl diphosphate and bisphenol S tetraphenyl disphosphate, and bisphenol F tetraphenyl diphosphate.

These esters having the general formula II wherein at least one of the groups R represents a group —OR (which includes all of the compounds having the general formulae III, IV, V, VI or VII) have the capacity to react with more than one molar proportion of an alcohol or phenol. The transesterification processes of this invention may be carried out in such a manner so as to replace all of these groups having the general formula —$OR_2$ or the processes may be carried out in a manner so as to replace only a proportion of these groups —$OR_2$ with a group —$OR_1$. Such partial transesterification may readily be achieved e.g. by terminating the reaction or by limiting the quantity of alcohol or phenol having the general formula $HOR_1$ used in the reaction. The products of the processes of this invention may comprise a product ester in which all of the $OR_2$ groups have been exchanged for $OR_1$ groups or a mixture of such esters with esters in which some but not all of the groups $OR_2$ have been exchanged for groups $OR_1$ and also possibly some unreacted ester having the formula II. In some instances it may be difficult to achieve complete transesterification within an acceptable time. The choice of catalyst may also exert an effect upon the degree of transesterification obtained for a particular reaction carried out under particular conditions. Where it is desired to maximise the degree of transesterification we have discovered that the use of a fluoride especially potassium fluoride as a catalyst is preferred.

The compound which is reacted with these esters may be any monohydric alcohol or polyhydric alcohol or a phenol, napthol or any other aromatic or heterocyclic compound having a hydroxyl group directly bonded to the aromatic or heterocyclic ring or mixtures thereof.

One preferred group of alcohols are primary aliphatic alcohols comprising from 1 to 24 carbon atoms per molecule. Particular examples of such alcohols include methanol, ethanol, propan-1-ol, n, iso or tertiary butanol, 2-methyl pentanol, 3-methyl pentanol, 2-ethylhexanol, octanol, nonanol, 1-decanol, isodecanol, 1-dodecanol, stearyl alcohol, 2-ethoxyethanol, tridecanol, tetradecanol, butoxyethanol, tribromoneopentyl alcohol, chloroethanol and chloro-propanol. Other alcohols which may be used include benzyl alcohol, furfuryl alcohol, allyl alcohol, diethylene glycol monobutyl ether and triethylene glycol monobutyl ether.

Another preferred group of alcohols are the aliphatic diols and polyols. Specific examples of such polyols include ethylene glycol, propylene glycol, neopentyl glycol, trimethylol propane, pentaerythritol, polyethylene glycol, polypropylene glycol and polytetrahydrofuran.

A third group of nucleophiles which are useful in the processes of this invention are monohydric and polyhydric phenols, napthols and other aromatic compounds having a hydroxyl substituent directly bonded to the aromatic ring and halogenated derivatives thereof. Particular examples which may be useful include resorcinol, catechol, bisphenol A, tetrabromo bisphenol A, tetrachloro bisphenol A, bisphenol F, bisphenol S, 1-napthol, 2-napthol and hydroquinone, phloroglucinol, 1,4-dihydoxy-napthalene, tertiary butyl phenols especially 2,4-ditertiarybutyl phenol, isopropylated phenols, butylated phenols, xylenols, cresols, and plant phenolics such as hydroxy flavanoids.

Processes which utilise a polyol or polyhydric phenol may result in the production of a product which comprises a complex mixture of phosphate esters. The processes may produce an ester which comprises an unreacted hydroxyl group. Alternatively these polyols may react with more than one phosphorus ester to produce a complex product mixture.

Another preferred embodiment of the invention comprises a transesterification process in which a mixture of more than one alcohol or phenol $HOR_1$ is used as a reactant. The product of such processes will comprise a mixture of phosphate esters the composition of which will vary with the nature of the alcohols or phenols and the relative proportions of the alcohols or phenols employed. The alcohols or phenols may be reacted simultaneously or sequentially. These processes may find application in the production of particular mixtures of phosphate esters having properties especially suited to particular applications. In general the reaction of the alcohols or phenols sequentially with the phosphate is preferable as such reactions are easier to control.

The transesterification processes of this invention may conveniently be carried out by heating the reactants at an elevated temperature usually one in the range 60 to 140° C. until the desired degree of reaction has occurred. Increasing the reaction temperature may result in the formation of a larger amount of by-product. The temperature at which any particular transesterification is carried out will be selected so as to balance the desire to increase the rate of the reaction by increasing the reaction temperature and the desire to reduce by-product formation. The reaction is carried out in the presence of an appropriate quantity of the catalyst.

Where the catalyst is dispersed in the reaction medium it will normally be effective when used in quantities of from 0.05 and more usually from 0.1 to 5.0 mole % of catalyst per mole of alcohol or phenol. In general the use of quantities in the range of 0.5 to 2.0 mole % of catalyst per mole of alcohol or phenol is preferred. Larger quantities of catalyst may be used but this is disadvantageous in so far as it increases the cost of the process and may present difficulties in separating it from the reaction product.

As noted above, the effective quantity of the catalyst may be limited by its solubility in the reaction medium. In a preferred embodiment an appropriate solvent is added to the reaction medium. Such a solvent will be selected so as to affect the transesterification reaction to the least possible extent. Such solvents will normally be needed in relatively small quantities and as a result some effect on the transesterification may be tolerable in view of the advantages achieved as a result of solubilising the catalyst. An example of a preferred solvent is phenol (and the alkylated derivatives thereof). Since phenols are generated during the reaction and means must be provided to separate them from the phosphate product the use of such phenols as a solvent is a preferred aspect of the invention as it does not require the introduction of a further separation step.

Where the catalyst is supported on a solid support and the reaction medium is brought into contact with that support the amount of catalyst may be much greater. Examples of supports upon which the catalyst may be mounted include alumina, silica, silica-alumina, calcium fluoride, celite and clays.

However the effective quantity will be of a similar order as that when the catalysed is dispersed throughout the reaction medium. The design of reaction systems which utilise catalysts mounted on a solid support is within the knowledge of the person skilled in the art. Such processes may be advantageous when used to manufacture products on a commercial basis and as such they represent a preferred aspect of this invention.

All the catalyst may be introduced into the reaction vessel at the start of the reaction or the catalyst may be added in aliquots during the course of the reaction. The reaction is preferably carried out under an inert atmosphere usually nitrogen so as to reduce the amount of byproduct formation. The reaction is preferably carried out under anhydrous conditions.

In a preferred embodiment the processes of this invention may also utilise a Lewis acid as a co-catalyst. Examples of such co-catalysts which have been found to be useful include magnesium chloride, aluminium chloride, dibutyltinoxide, tetrabutyl titanate, tetra-alkyl silicates such as silicon tetra-ethoxide and silicon tetrachloride.

The choice of catalyst system for any particular reaction will be influenced by a number of factors e.g., the activity of the catalyst, the ease with which it can be separated from the product and the ease with which it can be recovered and regenerated for re-use. All of those factors are within the knowledge of the person skilled in the art of catalysis and may be determined by routine experiment.

The reactants may be mixed in a wide range of proportions depending particularly upon the degree of reaction which is desired. Generally the ratio of the molar quantity of the alcohol or phenol to the second ester will be in the range of 0.5:1 to 1:1. Increasing the proportion of the alcohol or phenol will tend to increase the degree of the reaction under a given set of conditions. Successive addition of one or more alcohols or phenols may be used to synthesise particular products. The reaction may proceed to give substantially complete conversion of the phosphorus ester to its transesterified derivatives. Where the phosphorus ester contains more than one P—OR grouping as for example where the ester is phosphate, a thiophosphate, a phosphonate or a phosphoramidate all of these POR grouping are capable of undergoing reaction and the reaction may result in the complete conversion of these groups to their transesterified derivatives. The amount of alcohol of phenol should be increased in proportion to the degree of transesterification which is required.

The complete conversion of the phosphorus ester to its transesterified derivative may not be necessary or desirable. The partial transesterification of certain of the phosphorus esters produces a product comprising a mixture of esters which may in itself be useful. The products of the transesterification processes of this invention are organophosphorus compounds which find use in a variety of applications. They may for example be useful as plasticisers and flame retardants for plastics and resins, as additives for fuels and lubricants, as lubricating oils, as functional fluids, as antioxidants, as heat stabilisers and as chemical intermediates useful in the production of agrochemicals and pharmaceuticals.

The processes of this invention find particular application in the transesterification of phosphate esters. Products which comprise a mixture of triaryl phosphate, mono-alkyl diaryl phosphate, dialkylmonoaryl phosphate and trialkyl phosphate are articles of commerce and are sold for use e.g.; as flame retardant additives for polymeric materials and as functional fluids.

The progress of the transesterification processes of this invention may be monitored and controlled so as to produce a product comprising the desired mixture of esters. The reaction may be controlled by varying the nature of the catalyst, the quantity of the reactants or the duration of the reaction. Most conveniently the progress of the reaction may be monitored and the reaction terminated when the desired product has been produced. The reaction may be terminated either by removing the catalyst or by lowering the temperature of the reactants.

In a preferred procedure any unreacted alcohol or phenol is removed by distillation at the end of the reaction together with any remaining by-product alcohol or phenol. The catalyst or at least a proportion of it may be separated by filtration or washing out either before or after this distillation step.

In a preferred embodiment this invention provides processes for the reaction of a triaryl phosphate with an aliphatic alcohol to produce a trialkyl phosphate, a dialkyl monoaryl phosphate, a monoalkyl diaryl phosphate (or a product comprising a mixture of one or more of these materials) which is characterised in that these reactions are carried out in the presence of a catalytic quantity of a base having a base strength of less than 11 with the proviso that when the alcohol is 2-butoxy ethanol and the catalysy is a phenoxide the phenoxide is not initially reacted with the alcohol. Such processes are preferably carried out so as to produce a product comprising from 0 to 5.0 molar proportions of trialkyl phosphate,from 10 to 50 molar proportions of dialkyl monoaryl phosphate and from 40 to 80 molar proportions of monoalkyldiaryl phosphate.

The phosphate ester raw material is preferably a triaryl phosphate, most preferably triphenyl phosphate, a tris (isopropyl phenyl) phosphate, a tris (t-butyl phenyl) phosphate or a mixed pheny/isopropyl or phenyl/t-butyl phenyl phosphate or tricresyl phosphate or trixylyl phosphate. Mixtures of these various esters may also be useful.

A preferred class of reactants are the aliphatic alcohols. Most preferably the alcohol reactant is selected from the group comprising isodecanol, 2-ethylhexanol, 1-dodecanol, butoxyethanol, pentanol, isopentanol, butanol, isobutanol or ethanol.

In another preferred embodiment this invention provides processes for the total or partial transesterification of a triaryl phosphate by reaction with an alkylated phenol which is characterised in that the reaction is carried out in the presence of a catalytic quantity of a base having a base strength of less than 11. The phosphate ester starting materials are triphenyl phosphate, a tris (isopropyl phenyl) phosphate, a tris (tertiary butyl phenyl) phosphate, a mixed phenyl/isopropyl phenyl phosphate, a mixed phenyl/t-butyl phenyl phosphate, tricresyl phosphate or trixylyl phosphate. The alkylated phenols with which these phosphates are reacted are the alkylated phenols especially isopropyl phenol, tertiary butyl phenol, cresol, xylenol, resorcinol or hydroquinone (with the proviso that the phenolic reactant is not identical to the phenol which is produced by the transesterification reaction).

The preferred catalysts for use in the processes of this invention include potassium fluoride, cesium fluoride, potassium carbonate, ceasium carbonate, stannous fluoride, zinc acetate, potassium bicarbonate and potassium hexanoate.

In all the following examples the composition of the product was determined using phosphorus NMR and GC.

EXAMPLES

The abbreviations used in the tables are:

TPP—triphenyl phosphate
ADP—alkyldiphenyl phosphate
DAPP—dialkylphenyl phosphate
TAP—trialkyl phosphate
t/h—reaction time/hours

EXAMPLE 1

Triphenyl phosphate (600 g, 1.84 moles) isodecanol (727.0 g, 4.60 moles) and potassium fluoride (2.67 g, 0.046 moles) were heated at 100° C. under nitrogen for 9 hours. At this time excess isodecanol and phenol were removed by distillation at reduced pressure. A solid precipitated out at this point and was removed by filtration. Residual lights, mainly isodecanol and phenol, were removed and the final product distilled using a wiped film still at 0.02 to 0.03 mbar pressure, at temperatures of 100 and 140° C. respectively. 668.5 g (83.4%) of product (colourless liquid) was obtained at this point of composition (wt %) triphenyl phosphate (0.4%), isodecyl diphenyl phosphate (33.8%), diisodecyl phenyl phosphate (60.1%) and triisodecyl phosphate (5.8%). Most of the remaining 16.6% yield is associated with the catalyst on filtration.

EXAMPLE 2

As example 1 but using 2-ethylhexanol (956.4 g, 7.36 moles) and potassium fluoride (4.32 g, 0.074 moles) and heating for 12 h. 647.0 g (93.7%) product (colourless liquid) was obtained of composition (wt %) triphenyl phosphate (2.3%), 2-ethylhexyldiphenyl phosphate (61.9%, di-2-ethylhexylphenyl phosphate (33.6%) and tri-2-ethylhexyl phosphate (2.2%).

EXAMPLE 3

As example 1 but using triphenyl phosphate (300 g, 0.92 moles), 1-dodecanol (429 g, 2.3 moles) and potassium fluoride (1.34 g, 0.023 moles) and heating for 16h. 346.4 g (85%) product (colourless liquid) was obtained of composition (wt %) triphenyl phosphate (1.6%), dodecyldiphenyl phosphate (62.3%), didodecylphenyl phosphate (35.1%) and tridodecyl phosphate (0.9%).

EXAMPLES 4–9

Triphenyl phosphate (50 g, 0.153 moles), 2-ethylhexanol (50 g, 0.384 moles) and fluoride catalyst (1.0 mole % with respect to 2-ethylhexanol) were heated at 100° C. under $N_2$. Table 1 the product yields.

TABLE 1

| Example | Fluoride | T/H | Product Yields/Molar % | | |
|---|---|---|---|---|---|
| | | | TPP | ADP | DAPP |
| 4 | LIF | 9.25 | 0 | | |
| 5 | NaF | 9 | 0 | | |
| 6 | KF | 13.75 | 7 | 72 | 21 |
| 7 | RbF | 8 | 9 | 72 | 19 |
| 8 | CsF | 8 | 1 | 63 | 35 |
| 9 | KF—$Al_2O_3$ | 6.7 | 69 | 29 | 1 |

EXAMPLES 10–11

Triphenyl phosphate (50 G, 0.153 moles), 2-ethylhexanol (50 g, 0.384 moles) and potassium fluoride (0.22 g, 4 mmols) were heated at 75, 100 and 125° C. under nitrogen. Table 2 lists the product yields.

TABLE 2

| | | | Product Yields/Molar % | | |
|---|---|---|---|---|---|
| Example | T/° C. | t/h | TPP | ADP | DAPP |
| 10 | 75 | 8 | 63 | 35 | 191 |
| 11 | 125 | 8 | 8 | 70 | 19 |

EXAMPLES 12–13

Triphenyl phosphate (50 g, 0.153 moles), 2-ethylhexanol (50 g, 0.384 moles) and potassium fluoride (0.055 g, 1 mmol; 0.88 g, 16 mmol) were heated at 100° C. under nitrogen. Table 3 lists the product yields.

TABLE 3

| | | | Product Yields/Molar % | | |
|---|---|---|---|---|---|
| Example | c'yst mol % | t/h | TPP | ADP | DAPP |
| 12 | 0.25 | 15 | 27 | 65 | 8 |
| 13 | 4 | 12 | 2 | 64 | 30 |

EXAMPLES 14–15

Triphenyl phosphate (50 g, 0.153 moles), 2-ethylhexanol (30 g, 0.23 moles; 80 g, 0.61 moles) and potassium fluoride (1.0 mol % with respect to 2-ethylhexanol) were heated at 100° C. under nitrogen. Table 4 lists the product yields.

TABLE 4

| | Reactant Ratio | | Product Yields/Mole % | | |
|---|---|---|---|---|---|
| Example | TPP:2EH | t/h | TPP | ADP | DAPP |
| 14 | 1:1.5 | 11 | 41 | 54 | 5 |
| 15 | 1:4 | 11.25 | 0 | 53 | 45 |

EXAMPLES 16–18

These examples are given in Table 5, including reaction conditions.
(The alcohol ROH is isodecanol)

TABLE 5

| Example | Reaction Conditions | t/h | TPP | ADP | DAPP | TAP |
|---|---|---|---|---|---|---|
| | | | \multicolumn{4}{c}{Product Yields/Mol %} |
| 16 | 1:4 TPP:ROH<br>1 MOL % KF<br>100° C. | 9.25 | 0 | 24 | 66 | 9 |
| 17 | 1:2.5 TPP:ROH<br>1 MOL % KF<br>100° C. | 8.5 | 2 | 53 | 43 | 2 |
| 18 | 1:2.5 TPP:ROH<br>0.5 mol % KF<br>100° C. | 7.75 | 28 | 60 | 11 | <1 |

EXAMPLE 19

Reofos 50™(50 g, 0.136 moles), 1-dodecanol (63.5 g, 0.34 moles) and potassium fluoride (0.20 g, 0.0034 moles) were charged to a 250 ml vessel and heated for 10 h at 100° C. under nitrogen. At this time $^{31}$P nmr indicated a product mixture comprising triarylphosphate (6.8 mol %), dodecyldiaryl phosphate (52.7%), didodecylaryl phosphate (37.4%) and tridodecyl phosphate (3.0%).

Reofos 50 is a mixture of various phenyl and isopropylated phenyl phosphate.

EXAMPLE 20

Reofos 50 (50 g, 0.136 moles), isodecanol (53.7 g, 0.34 moles) and potassium fluoride (0.20 g, 0.0034 moles) were charged to a 250 ml vessel and heated for 10 h at 100° C. under nitrogen. At this time $^{31}$P nmr indicated a product mixture comprising triaryl phosphate (8.3 mol %), isodecyldiaryl phosphate (55.8%), diisodecylaryl phosphate (32.5%) and triisodecyl phosphate (3.3%).

EXAMPLE 21

Reofos 50 (50 g, 0.136 moles), 2-ethylhexanol (71.0 g, 0.55 moles) and potassium fluoride (0.32 g, 0.0055 moles) were charged to a 250 ml vessel and heated for 10 h at 100° C. under nitrogen. At this time $^{31}$P nmr indicated a product mixture comprising triaryl phosphate (8.5 mol %), 2-ethylhexyldiaryl phosphate (62.6%), di-2-ethylhexylaryl phosphate (28.8%) and tri-2-ethylhexyl phosphate (1.6%).

EXAMPLE 22

Triphenyl phosphate (50 g, 01.5 moles), ethylene glycol (47.6 g, 0.77 moles) and potassium fluoride (0.46 g, 0.0077 moles) were charged to a 250 ml vessel and heated for 1 h at 100° C. under nitrogen. At this time $^{31}$P nmr indicated a product mixture comprising 5 membered ring cyclic phosphates (7 mol %) trialkyl phosphates (88%), arylalkyl phosphates (2%) and triphenyl phosphate (3%).

EXAMPLE 23

Triphenyl phosphate (50 g, 0.15 moles), neopentyl glycol (47.6 g, 0.77 moles) and potassium fluoride (0.22 g, 3.8 mmoles) were charged to a 250 ml vessel and heated to 5 h at 100° C. under nitrogen. At this time $^{31}$P nmr indicated a product mixture comprising triphenyl phosphate (4.3 mol %), phenyl neopentyl glyclyl phosphate (89.2%) and 3-hydroxy-2, 2-dimethylpropyl neopentylglycyl phosphate (6.4%).

EXAMPLE 24

Tris (2,4-dibromophenyl) phosphate (101.3 g, 0.13 moles), isodecanol (50 g, 0.32 moles) and potassium fluoride (0.36 g, 64 mmoles) were heated to 120° C. for 12 h under nitrogen. At this time $^{31}$P nmr indicated a product mixture comprising tris (2,4-dibromophenyl) phosphate 6.4 mol %; isodecyl bis 2,4 dibromophenyl phosphate 53.6%, diisodecyl 2-4-dibromophenyl phosphate (33.6%) and triisodecyl phosphate (6.4%).

EXAMPLE 25

Triphenyl phosphate (400 g, 1.23 moles), resorcinol (67.7 g, 0.62 moles) and potassium fluoride (0.35 g, 62 mmoles) were heated to 140° C. under 5 mmHg pressure with steady distillation of phenol for 4 h yielding 128.4 g distillate (phenol) and 325 g product comprising triphenyl phosphate (45.5%), resorcinol tetraphenyl diphosphate (29.5%), resorcinol diphenyl phosphate (6.2%), diresorcinol pentaphenyl diphosphate (2.1%), diresorcinol triphenyl diphosphate (4.1%), triresorcinol hexaphenyl tetraphosphate (12.3%), triresorcinol tetraphenyl triphosphate (0.3%).

EXAMPLE 26

Triphenyl phosphate (12.4 g, 38.2 mmols), butoxyethanol (45.1 g, 0.38 mols) and potassium fluoride (0.22 g, 3.8 mmols) were charged to a 250 ml flask and heated to 125° C. for 7 h, whereupon $^{31}$P nmr indicated 98% conversion to tributoxyethyl phosphate.

EXAMPLE 27

Triphenyl phosphate (100 g, 0.31 mols), 1-butanol (226.8 g, 3.06 mols) and potassium fluoride (3.55 g, 30.6 mmols) were charged to a 1 liter flask under nitrogen and heated at reflux for 4.5 h. At this point $^{31}$P nmr indicated conversion to tributyl phosphate and dibutylphenyl phosphate in a ratio of approximately 50:50.

EXAMPLE 28

Triphenyl phosphate (12.4 g, 38.2 mmol), absolute ethanol (18.0 g, 0.38 mol) and potassium fluoride (0.22 g, 3.8 mmol) were charged to a 250 ml flask under nitrogen and heated at reflux under nitrogen for 8 h. At this point $^{31}$P nmr indicated a product mixture containing triethyl phosphate, diethylphenyl phosphate and ethyldiphenyl phosphate in a ratio of 1.2:6.8:1.

EXAMPLE 29

Triphenylphosphate (500 g, 1.53 moles), 2-ethylhexanol (1798 g, 13.8 mols) and potassium fluoride (8.0 g, 0.138 moles) were charged to a 5 litre vessel under nitrogen and heated at 100° C. for 10 h. Excess 2-ethylhexanol and phenol were stripped at 70–90° C. and 0.1 mbar to yield 592 g product of composition triphenyl phosphate (0.5 mol %), 2-ethylhexyl diphenyl phosphate (48.8%, di-2-ethylhexylphenyl phosphate (46.1%) and tri-2-ethylhexyl phosphate (4.4%). To this was charged butoxyethanol (1675 g, 14.0 moles) and the reaction mixture heated to 100° C. under nitrogen for a further 6 h, and finally heated to 125° C. for a further 6 h. Excess butoxyethanol and phenol were stripped at 80° C. and 0.08 mbar, the catalyst filtered off to leave 577 g colourless liquid containing 90% mixed trialkyl phosphates.

EXAMPLE 30

Triphenyl phosphate (50 g, 0.16 mols), isodecanol (63.7 g, 0.4 mols) and potassium fluoride (0.023 g, 4 mmols) were heated to 100° C. under nitrogen for 1 h. Whereupon $^{31}$P nmr indicated the formation of isodecyldiphenyl phosphate, diisodecylphenyl phosphate and triisodecyl phosphate in the molar ration 1:5.5:5.3.

EXAMPLE 31

Triphenyl phosphate (50 g, 0.16 moles), isodecanol (36.3 g, 0.23 moles) and potassium carbonate (0.74 g, 0.0023 moles) were heated to 100° C. under nitrogen for 4 h. At this point $^{31}$P nmr indicated the formation of a mixture containing TPP (11 mole %) ADP (74%) and DAPP (10%).

EXAMPLE 32

Triphenyl phosphate (50 g, 0.16 moles), isodecanol (36.3 g, 0.23 moles) and zinc acetate dihydrate (1.28 g, 0.0023 moles) were heated to 100° C. under nitrogen for 4 h. At this point $^{31}$P nmr indicated the formation of a mixture containing TPP (41 mole %), ADP (56%) and DAPP (3%).

EXAMPLE 33

Triphenyl phosphate (50 g, 0.16 moles), isodecanol (36.3 g, 0.23 moles) and cesium carbonate (0.75 g, 0.0023 moles) were heated to 100° C. under nitrogen for 2 h. At this point $^{31}$P nmr indicated the formation of a mixture containing TPP (62 mole %), ADP (36%) and DAPP (1%).

EXAMPLES 33–41

Triphenylphosphate (50 g, 0.153 moles), isodecanol (49.0 g, 0.31 moles) were heated together in the presence of various catalysts and catalyst combinations at 100° C. under N$_2$. The catalyst details with result are given in Table 6.

TABLE 6

| Example | Catalyst(s) | Mole % wrt ROH | t/h | TPP | ADP | DAPP | TAP |
|---|---|---|---|---|---|---|---|
| 33 | K$_2$CO$_3$: DMAP | 1:0.25 | 5 | 13 | 76 | 11 | |
| 34 | K$_2$CO$_3$: MgCl$_2$ | 0.5:0.5 | 4 | 15 | 75 | 10 | |
| 35 | K$_2$CO$_3$: MgCl$_2$ | 0.9:0.1 | 4 | 10 | 71 | 16 | |
| 36 | KF:Et$_3$ | 1:0.25 | 5 | 23 | 63 | 13 | |
| 37 | KF:DMAP | 1:0.25 | 5 | 8 | 67 | 24 | 1 |
| 38 | Potassium acetate | 1.0 | 6 | 87 | 12 | | |
| 39 | Potassium heptanoate | 1.0 | 6 | 55 | 42 | 2 | |
| 40 | KHCO$_3$ | 1.0 | 8 | 67 | 32 | 1 | |
| 41 | Na$_2$CO$_3$ | 1.0 | 8 | 94 | 6 | | |

EXAMPLES 42–48

Triphenylphosphate (200 g, 0.61 moles) and resorcinol (67.1 g, 0.61 moles) and potassium carbonate were charged to a 500 ml 4-neck flask fitted for distillation using a distillation head, thermometer and liebig condenser (attached to a water circulator) fitted to a 100 ml receiver flask.

EXAMPLES 42–43 are shown in Table 7, in which the reaction mixture was heated to 110° C. and 140° C. respectively. 1.0 mole % (wrt resorcinol) potassium carbonate used.

EXAMPLES 44–46 are shown in Table 8, in which various levels of potassium carbonate catalyst were used, and the reaction mixture heated to 110° C. under a vacuum of 10 mmHg with a nitrogen flow of 250 cm$^3$ min.

EXAMPLES 47–48 are shown in Table 9, in which sodium carbonate and rubidium carbonate (1 wt % wrt resorcinol) are used as catalysts, with the reaction mixture heated at 110° C. under atmospheric pressure.

TABLE 7

| EXAMPLE 42 110° C. | | | | | | |
|---|---|---|---|---|---|---|
| Time Hrs | TPP-OH % | Unit 1-OH % | Unit 2-OH % | TPP % | Resorcinol % | Phenol % |
| 1 | 16.4 | 0.6 | 0.0 | 59.1 | 15.9 | 2.9 |
| 2 | 20.4 | 1.8 | 0.1 | 53.5 | 14.3 | 4.9 |
| 3 | 27.6 | 2.9 | 0.3 | 45.5 | 12.3 | 6.7 |
| 4 | 29.1 | 3.7 | 0.4 | 41.9 | 11.2 | 8.0 |
| 5 | 30.2 | 3.5 | 0.4 | 39.2 | 11.8 | 10.1 |

| EXAMPLE 43 140° C. | | | | | | |
|---|---|---|---|---|---|---|
| Time Hrs | TPP-OH % | Unit 1-OH % | Unit 2-OH % | TPP % | Resorcinol % | Phenol % |
| 1 | 34.2 | 6.4 | 1.0 | 30.5 | 7.8 | 14.3 |
| 2 | 33.1 | 8.6 | 1.8 | 21.0 | 4.1 | 14.6 |
| 3 | 31.1 | 9.8 | 2.4 | 18.1 | 3.3 | 13.1 |
| 4 | 29.5 | 10.6 | 2.9 | 16.7 | 2.6 | 10.7 |
| 5 | 26.5 | 11.3 | 3.8 | 14.9 | 2.1 | 8.9 |

TPP = triphenylphosphate
TPPOH = 3-hydroxyphenyl phosphate
Unit 1-OH = ααβ-triphenyl-αβ-resorcyl-β-3-hydroxyphenyl disphosphate
Unit 2-OH = oligomer, P$_3$ analogue of Unit 1 OH

TABLE 8

| EXAMPLE 44 1% POTASSIUM CARBONATE | | | | | | |
|---|---|---|---|---|---|---|
| Time Hrs | TPP-OH % | Unit 1-OH % | Unit 2-OH % | TPP % | Resorcinol % | Phenol % |
| 1 | 23.0 | 1.0 | 0.0 | 54.0 | 13.6 | 3.3 |
| 2 | 30.9 | 2.3 | 0.2 | 43.0 | 12.2 | 5.8 |
| 3 | 34.5 | 3.2 | 0.3 | 37.9 | 11.6 | 7.5 |
| 4 | 36.2 | 3.1 | 0.4 | 34.0 | 11.2 | 8.9 |
| 5 | 38.3 | 3.1 | 0.5 | 32 | 10.5 | 10.7 |

| EXAMPLE 45 0.5% POTASSIUM CARBONATE | | | | | | |
|---|---|---|---|---|---|---|
| Time Hrs | TPP-OH % | Unit 1-OH % | Unit 2-OH % | TPP % | Resorcinol % | Phenol % |
| 1 | 11.2 | 0.3 | 0.0 | 56.4 | 15.2 | 11.9 |
| 2 | 19.1 | 1.0 | 0.8 | 56.8 | 16.2 | 1.9 |
| 3 | 22.6 | 1.5 | 0.1 | 53.0 | 15.6 | 2.2 |
| 4 | 26.3 | 2.36 | 0.2 | 49.6 | 15.2 | 1.4 |
| 5 | 29.3 | 3.33 | 0.3 | 46.0 | 14.3 | 1.6 |

| EXAMPLE 46 0.25% POTASSIUM CARBONATE | | | | | | |
|---|---|---|---|---|---|---|
| Time Hrs | TPP-OH % | Unit 1-OH % | Unit 2-OH % | TPP % | Resorcinol % | Phenol % |
| 1 | 6.1 | 0.0 | 0.0 | 70.2 | 17.8 | 0.8 |
| 2 | 9.1 | 0.1 | 0.0 | 67.5 | 17.3 | 0.9 |
| 3 | 12.0 | 0.3 | 0.0 | 64.6 | 17.1 | 0.9 |
| 4 | 15.1 | 0.6 | 0.0 | 61.3 | 16.6 | 1.4 |
| 5 | 19.0 | 0.9 | 0.0 | 57.8 | 16.3 | 0.9 |

TABLE 9

EXAMPLE 47
1% SODIUM CARBONATE

| Time Hrs | TPP-OH % | Unit 1-OH % | Unit 2-OH % | TPP % | Resorcinol % | Phenol % |
|---|---|---|---|---|---|---|
| 1 | 0.0 | 0.0 | 0.0 | 80.0 | 20.0 | 0.0 |
| 2 | 1.5 | 0.0 | 0.0 | 75.4 | 17.9 | 0.2 |
| 3 | 2.9 | 0.0 | 0.0 | 74.2 | 17.5 | 0.4 |
| 4 | 4.6 | 0.0 | 0.0 | 72.5 | 17.4 | 0.5 |
| 5 | 6.1 | 0.0 | 0.0 | 71.1 | 17.1 | 0.7 |

EXAMPLE 48
1% RUBIDIUM CARBONATE

| Time Hrs | TPP-OH % | Unit 1-OH % | Unit 2-OH % | TPP % | Resorcinol % | Phenol % |
|---|---|---|---|---|---|---|
| 1 | 11.2 | 0.2 | 0.0 | 65.4 | 16.3 | 1.8 |
| 2 | 18.7 | 0.8 | 0.0 | 57.1 | 15.0 | 3.4 |
| 3 | 21.8 | 1.2 | 0.0 | 53.4 | 14.4 | 4.1 |
| 4 | 24.7 | 1.7 | 0.0 | 49.8 | 13.7 | 5.1 |
| 5 | 26.4 | 2.1 | 0.2 | 47.4 | 13.3 | 5.8 |

EXAMPLE 49

Triphenylphosphate (50 g, 0.15 moles), 2-isopropyl phenol (62.5 g, 0.45 moles) and potassium carbonate (0.5 g) were heated at 120° C. under nitrogen for 2 h to give a mixture comprising triphenylphosphate (10 wt %), diphenyl 2-isopropylphenyl phosphate (43%), phenyl di(2-isopropylphenyl) phosphate (41%), and tris(isopropylphenyl) phosphate (6%).

EXAMPLE 50

Triphenyl phosphate (50 g, 0.15 moles), 4-tert-butyl phenol (68.5 g, 0.45 moles) and potassium carbonate (0.5 g) were heated at 120° C. under nitrogen for 1 h to give the mixture comprising, triphenyl phosphate (11 wt %), diphenyl 4-t-butyl phenylphosphate (38%) and tri(4-t-butyl phenyl phosphate (19%).

EXAMPLE 51

As example 50 using potassium fluoride (0.5 g) and heating at 100° C. at 2 h under nitrogen to give a mixture comprising, triphenylphosphate (14 wt %), diphenyl 4-t-butyl phenylphosphate (28%), phenyl di(4-t-butyl phenyl) phosphate (40%) and tri (4-t-butyl phenyl) phosphate (18%).

EXAMPLE 52

Triphenyl phosphate (300 g, 0.92 moles), n-butanol (68 g, 9.19 moles) and potassium fluoride (5.3 g) were charged to a 3 litre flask and heated at 110° C. under nitrogen for 12 h. Excess butanol and phenol were removed by distillation at reduced pressure. The resulting material was filtered and purified by short path distillation to give a product mixture containing tributylphosphate (43 mol %) and dibutyl phenylphosphate (57 mol %) in an overall yield of over 90%.

EXAMPLE 53

Triphenyl phosphate(200 g, 0.61 moles), iso-butanol (363 g, 4.9 moles) and potassium fluoride (2.85 g) were charged to a 2 litre flask and heated at reflux for 19 h. Excess isobutanol and phenol were removed by distillation at reduced pressure. The resulting material was filtered and purified by short path distillation to give a product containing triisobutyl phosphate (56 mol %) and diisobutyl phenyl phosphate (44 mol %) in an overall yield of greater than 90%.

What we claim is:

1. A process for the production of a phosphate ester product comprising a trialkyl phosphate, a dialkyl monoaryl phosphate, an alkyl diaryl phosphate, or a mixture thereof, the process comprising transesterifing a triaryl phosphate with an aliphatic alcohol in the presence of a catalytic quantity of a base having a base strength of less than 11, in which the base is a hexanoate, an amine, an acetate, a carbonate, a bicarbonate, a phosphite, a hypophosphite, a phosphate, a tungstate, a fluoride, or an oxide.

2. The process of claim 1 in which the base has a base strength in the range of 3 to 8.

3. The process of claim 1 in which the base is an acetate, a carbonate, a bicarbonate, or a fluoride.

4. The process of claim 1 in which the base is selected from the group consisting of potassium fluoride, rubidium fluoride, cesium fluoride, potassium-carbonate, cesium carbonate, ammonium carbonate, barium carbonate, strontium carbonate, lanthanum carbonate, cerium carbonate, potassium acetate, potassium hexanoate, zinc acetate, cupric acetate, stannous acetate, sodium hypophosphite, potassium hypophosphite, calcium phosphate, calcium oxide, magnesium oxide, nickel oxide, strontium oxide, hydroxyapatite, ethylamine, diethylamine, dimethylamine, pyridine, pyrollidine, piperidine, morpholine, quinoline, quinuclidine, DABCO, DBU and DBN.

5. The process of claim 1 in which the base is selected from the group consisting of potassium fluoride, cesium fluoride, potassium carbonate, potassium bicarbonate, cesium carbonate, stannous fluoride, zinc acetate, and potassium hexanoate.

6. The process of claim 1 in which the base is present in a quantity of from 0.05 to 5.0 mole % per mole of alcohol.

7. A process for the production of a phosphate ester product comprising a trialkyl phosphate, a dialkyl monoaryl phosphate, an alkyl diaryl phosphate, or a mixture thereof, the process comprising transesterifing a triaryl phosphate with an aliphatic alcohol in the presence of a catalytic quantity of a base having a base strength of less than 11 in which the process is carried out in the presence of a Lewis acid co-catalyst.

8. The process of claim 7 in which the co-catalyst is selected from the group consisting of magnesium chloride, aluminum chloride, dibutyl tin oxide, tetra-butyl titanate, tetra-alkyl silicates, and silicon tetrachloride.

9. The process of claim 8 in which the base is fluoride.

10. The process of claim 7 in which the base has a base strength in the range of 3 to 8.

11. The process of claim 7 in which the base is selected from the group consisting of amines, acetates, carbonates, fluorides, bicarbonates, tungstates, oxides, and hexanoates.

12. The process of claim 11 in which the base is selected from the group consisting of acetates, carbonates, fluorides, bicarbonates, and potassium hexanoate.

13. The process of claim 11 in which the base is selected from the group consisting of potassium fluoride, potassium carbonate, stannous fluoride, zinc acetate, potassium bicarbonate, and potassium hexanoate.

14. The process of claim 13 in which the triaryl phosphate is selected from the group consisting of triphenyl phosphate, tris(iso-propyl phenyl) phosphate, tris(t-butyl phenyl) phosphate, mixed phenyl/iso-propyl phenyl phosphate, mixed phenyl/t-butyl phenyl phosphate, tricresyl phosphate, trixylyl phosphate, and mixtures thereof.

15. The process of claim 14 in which the aliphatic alcohol is selected from the group consisting of iso-decanol, 2-ethylhexanol, 1-dodecanol, butoxyethanol, pentanol, iso-pentanol, butanol, iso-butanol, and ethanol.

16. The process of claim 15 in which the base is a fluoride.

17. The process of claim 15 in which the process is carried out at a temperature in the range of 60° C. to 140° C.

18. The process of claim 17 in which the base is present in a quantity of from 0.05 to 5.0 mole % per mole of alcohol.

19. The process of claim 12 in which the product comprises from 0 to 50 mole % of trialkyl phosphate, from 10 to 50 mole % of dialkylmonoaryl phosphate and from 40 to 80 mole of monoalkyldiary phosphate.

20. The process of claim 11 in which the base is a fluoride.

21. The process of claim 7 in which the Lewis acid co-catalyst is selected from the group consisting of magnesium chloride, aluminum chloride, dibutyl tin oxide, tetra-butyl titanate, tetra-alkyl silicates, and silicon tetrachloride.

22. The process of claim 21 in which the base is a fluoride.

23. The process of claim 7 in which the base is present in a quantity of from 0.05 to 5.0 mole % per mole of alcohol.

24. The process of claim 1 in which the process is carried out at a temperature in the range of 60° C. to 140° C.

25. The process of claim 1 in which the triaryl phosphate is selected from the group consisting of triphenyl phosphate, tricresyl phosphate, cresyl diphenyl phosphate, trixylyl phosphate, tris (iso-ropyl phenyl) phosphate, tris(t-butyl phenyl) phosphate, mixtures of triaryl phosphates that have been produced by the reaction of phosphorous oxychloride with a mixture of phenols and alkylated phenols, and tris (2,4-dibromo phenyl) phosphate.

26. The process of claim 1 in which the aliphatic alcohol comprises from 1 to 24 carbon atoms.

27. The process of claim 26 in which the aliphatic alcohol is selected from the group consisting of methanol, ethanol, propanol, n-butanol, iso-butanol, tertiary butanol, 2-methyl pentanol, 3-methyl pentanol, 2-ethylhexanol, octanol, nonanol, 1-decanol, iso-decanol, 1-dodecanol, stearyl alcohol, 2-ethoxy ethanol, tridecanol, tetradecanol, butoxyethanol tribromopentyl alcohol, chloroethanol, choloropropanol, benzyl alcohol, furfuryl alcohol, allyl alcohol, diethylene glycol monobutyl ether, and triethylene glycol monobutyl ether.

28. The process of claim 26 in which the aliphatic alcohol comprises from 6 to 18 carbon atoms.

29. The process of claim 28 in which the aliphatic alcohol is selected from the group consisting of 2-ethylhexanol, iso-decanol, and dodecanol.

30. The process of claim 1 in which the product comprises from 0 to 50 mole % of trialkyl phosphate, from 10 to 50 mole % of dialkylmonoaryl phosphate and from 40 to 80 mole % of monoalkyldiary phosphate.

31. The process of claim 1 in which the triarylphosphate is triphenyl phosphate.

32. The process of any of claims 1–6, 24, 25–26, 10, and 30–29 in which the base is potassium fluoride.

* * * * *